US008962261B2

(12) United States Patent
Sarwal et al.

(10) Patent No.: US 8,962,261 B2
(45) Date of Patent: Feb. 24, 2015

(54) AUTOANTIBODY BIOMARKERS FOR IGA NEPHROPATHY

(75) Inventors: Minnie M. Sarwal, Portola Valley, CA (US); Tara Sigdel, Palo Alto, CA (US); Sang H. Woo, Stanford, CA (US); Richard Lafayette, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/001,827

(22) PCT Filed: Apr. 6, 2012

(86) PCT No.: PCT/US2012/032609
§ 371 (c)(1),
(2), (4) Date: Feb. 5, 2014

(87) PCT Pub. No.: WO2012/139051
PCT Pub. Date: Oct. 11, 2012

(65) Prior Publication Data
US 2014/0141449 A1  May 22, 2014

Related U.S. Application Data

(60) Provisional application No. 61/472,408, filed on Apr. 6, 2011.

(51) Int. Cl.
*G01N 33/53* (2006.01)
*G01N 33/68* (2006.01)
*G01N 33/564* (2006.01)

(52) U.S. Cl.
CPC .......... *G01N 33/6854* (2013.01); *G01N 33/564* (2013.01); *G01N 33/6893* (2013.01); *G01N 2800/347* (2013.01)
USPC ............................................. 435/7.1; 435/7.2

(58) Field of Classification Search
None
See application file for complete search history.

(56) References Cited

U.S. PATENT DOCUMENTS

| | | | |
|---|---|---|---|
| 6,607,879 | B1 | 8/2003 | Cocks et al. |
| 7,026,121 | B1 | 4/2006 | Wohlgemuth et al. |
| 7,879,556 | B2 | 2/2011 | Wohlgemuth et al. |
| 2003/0017619 | A1 | 1/2003 | Rokubo et al. |
| 2003/0104371 | A1 | 6/2003 | Strom et al. |
| 2004/0163654 | A1 | 8/2004 | Williams |
| 2006/0088836 | A1 | 4/2006 | Wohlgemuth et al. |
| 2006/0088876 | A1 | 4/2006 | Bauer |
| 2006/0246485 | A1 | 11/2006 | Sarwal et al. |
| 2006/0269949 | A1 | 11/2006 | Halloran et al. |
| 2006/0281122 | A1 | 12/2006 | Bryant et al. |
| 2007/0031890 | A1 | 2/2007 | Wohlgemuth et al. |
| 2007/0111210 | A1 | 5/2007 | Bigaud et al. |
| 2007/0122806 | A1 | 5/2007 | Strom et al. |
| 2007/0134728 | A1 | 6/2007 | Hu et al. |
| 2007/0212701 | A1 | 9/2007 | O'Toole et al. |
| 2007/0232658 | A1 | 10/2007 | Wagner et al. |
| 2007/0264272 | A1 | 11/2007 | Perreault et al. |
| 2008/0233573 | A1 | 9/2008 | Storm et al. |
| 2009/0022730 | A1 | 1/2009 | Raulf et al. |
| 2009/0197286 | A1 | 8/2009 | Karin et al. |
| 2009/0269334 | A1 | 10/2009 | Bigaud et al. |
| 2009/0304705 | A1 | 12/2009 | Grass |
| 2010/0120629 | A1 | 5/2010 | Ellis et al. |
| 2011/0201519 | A1 | 8/2011 | Sarwal et al. |
| 2013/0157888 | A1 | 6/2013 | Nagele |

FOREIGN PATENT DOCUMENTS

| | | |
|---|---|---|
| EP | 1731620 | 12/2006 |
| EP | 2295966 | 3/2011 |
| WO | 2004/074815 | 9/2004 |
| WO | 2005/005601 | 1/2005 |
| WO | 2005/070086 | 8/2005 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | 2010/038974 | 8/2010 |

OTHER PUBLICATIONS

Nesslinger et al. (Clinical Cancer Research 2010 vol. 16, p. 4046-4056).*
Agilent-014850 whole human genome microarray 4x44K G4112F (Probe Name Version), GEO (2008), XP002594592.
Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.
Akalin; et al., "Gene expression analysis in human renal allograft biopsy samples using high-density oligoarray technology", Transplantation (2001), 72(5):948-53.
Alarcon; et al. "Time to renal disease and end-stage renal disease in PROFILE: a multiethnic lupus cohort", PLos Med (Oct. 2006), 3(10):e396.
Braud; et al., "Immunosuppresive Drug-Free Operational Immune Tolerance in Human Kidney Transplant Recipients: Part 1. Blood Gene Expression Statistical Analysis", Journal of Cellular Biochemistry (Apr. 2008),103(6):1681-1692.

(Continued)

*Primary Examiner* — Jacob Cheu
(74) *Attorney, Agent, or Firm* — Bozicevic, Field & Francis LLP; Bret E. Field

(57) ABSTRACT

Aspects of the present invention include methods for diagnosing and monitoring IgAN in a subject. In practicing one aspect of the subject methods, a sample from a subject is analyzed for the presence of one or more specific autoantibodies to determine the IgAN phenotype of the subject. Also provided are compositions, systems, kits and computer program products that find use in practicing the subject methods. The methods and compositions find use in a variety of applications.

12 Claims, 6 Drawing Sheets

(56) References Cited

OTHER PUBLICATIONS

Brouard; et al., "Identification of a peripheral blood transcriptional biomarker panel associated with operational renal allograft tolerance", PNAS (2007), 104(39):15448-15453.

Butte; et al., "Protein microarrays discover angiotensinogen and PRKRIP1 as novel targets for autoantibodies in chronic renal disease", Mol Cell Proteomics (Mar. 2011), 10(3):M110.000497.

Carvalho-Gaspar; et al., "Chemokine gene expression during allograft rejection: Comparison of two quantitative PCR techniques", Journal of Immunological Methods (2005), 301(1-2):41-52.

Chan, "Integrating Transcriptomics and Proteomics", Drug Discovery and Development (Apr. 2006), printed from www.ddmag.com, 6 pages.

Chen; et al., "Discordant protein and mRNA expression in lung adenocarcinomas", Molecular and Cellular Proteomics (2002), 1(4):304-13.

Cheung; et al., "Natural Variation in Human Gene Expression Assessed in Lymphoblastoid Cells," Nature Genetics (Mar. 2003), 33:422-425.

Chu; et al., "Cloning of a new "finger" protein gene (ZNF173) within the class I region of the human MHC", Genomics (1995), 29(1):229-39.

Chua; et al., "Applications of Microarrays to Renal Transplantation: Progress and Possibilities" Frontiers in Bioscience (2003), 8:S913-23.

Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.

Cox; et al., "Altered modulation of WNT-beta-catenin and PI3K/Akt pathways in IgA nephropathy", Kidney Int (Aug. 2010), 78(4):396-407.

Database Embl [Online], "Thymidine Kinase, Cytosolic (human), mRNA Sequence", (Feb. 1998), 2pages, XP002434108, Database accession No. AA778098.

Dinarello; et al., "Anti-inflammatory Agents: Present and Future", Cell (Mar. 2010), 140(6):935-950.

Dugré; et al., "Cytokine and cytotoxic molecule gene expression determined in peripheral blood mononuclear cells in the diagnosis of acute renal rejection.", Transplantation (2000), 70(7):1074-1080.

Enard; et al., "Intra- and interspecific variation in primate gene expression patterns", Science (Apr. 2002), 296 (5566):340-3.

Farivar; et al., "The role of CC and CXC chemokines in cardiac allograft rejection in rats", Experimental and Molecular Pathology (2005), 78(3):171-176.

Flechner; et al., "Kidney transplant rejection and tissue injury by gene profiling of biopsies and peripheral blood lymphocytes", American Journal of Transplantation (2004), 4(9):1475-89.

Fujiwaki; et al., "Thymidine Kinase in Epitheliar Ovarian Cancer: Relationship with the Other Pyrimidine Pathway Enzymes", Int. J. Cancer (2002), 99(3):328-335.

Gimino; et al., Gene Expression Profiling of Broncholveolar Lavage Cells in Acute Lung Rejection, American Journal of Respiratory and Critical Care Medicine (2003), 168:1237-1242.

Gronowitz; et al., "Serum Thymidine Kinase in Transplant Patients: Its Relation to Cytomegalovirus Activity, Renal Transplant Rejection and its Use for Monitoring of Antiviral Therapy", Annals of Clinical Research (1986), 18(2):71-75.

Gwinner; et al. "Renal transplant rejection markers." World J Urol (Oct. 2007), 25(5):445-455.

Hauge; et al., "Characterization of the FAM110 gene family", Genomics (May 2007), 90:14-27.

Hernandez-Fuentes; et al., "Immunologic monitoring", Immunological Reviews (2003), 196:247-264.

Hillier; et al., "Generation and annotation of the DNA sequences of human chromosomes 2 and 4", Nature (2005), 434:724-731.

Horwitz; et al., "Detection of Cardiac Allograft Rejection and Response to Immunosuppressive Therapy with Peripheral Blood Gene Expression," Circulation (2004), 110:3815-3821.

Ismail; et al., "Important fluorinated drugs in experimental and clinical use", Journal of Fluorine Chemistry (Dec. 2002), 118(1):27-33.

Jevnikar; et al., "Late Kidney Allograft Loss: What We Know About It, and What We Can Do About It", Clin J Am Soc Nephrol (2008), 3(S56-S67).

Joosten; et al., "Chronic Renal Allograft Rejection: Pathophysiologic Considerations", Kidney International (2005), 68:1-13.

Kalil; et al., "Meta-analysis: the efficacy of strategies to prevent organ disease by cytomegalovirus in solid organ transplant recipients", Ann Intern Med (Dec. 2005), 143(12):870-880.

Kaposztas; et al., "Impact of rituximab therapy for treatment of acute humoral rejection", Clin Transplant (Jan.-Feb. 2009), 23(1):63-73.

Lang; et al. "DUSP meet immunology: dual specificity MAPK phosphatases in control of the inflammatory response", J Immunol (Dec. 2006), 177(11):7497-504.

Lee et al., "Expression profiling of murine double-negative regularoty T cells suggest mechanisms for prolonged cardiac allograft survival", J. Immunol. (2005), 174(8):4535-4544.

Li; et al. "A Peripheral Blood Diagnostic Test for Acute Rejection in Renal Transplantation", American Journal of Transplantation (Oct. 2012), 12(10):2710-2718.

Li; et al., "Identifying compartment-specific non-HLA targets after renal transplantation by integrating transcriptome and "antibodyome" measures", PNAS (2009), 106(11):4148-4153.

Ling; et al. "Integrative urinary peptidomics in renal transplantation identifies biomarkers for acute rejection", J Am Soc Nephrol (Apr. 2010), 21(4):646-653.

Mansfield; et al., "Arraying the Orchestration of Allograft Pathology", American Journal of Transplantation (2004), 4 (6):853-62.

Marsden, "Predicting Outcomes after Renal Transplantation- New Tools and Old Tools," The New England Journal of Medicine (2003), 349(2):182-184.

Martinez-Llordella; et al., "Using transcriptional profiling to develop a diagnostic test of operational tolerance in liver transplant recipients", The Journal of Clinical Investigations (Aug. 2008), 118(8):2845-2857.

Matsuki; et al., "Novel regulation of MHC class II function in B cells", The EMBO Journal (Jan. 2007), 26:846-854.

McMorrow; et al., "New intra-renal graft genes associated with tolerance or rejection", Kidney International, symp. 1 (2002), 61: S85-S93.

Medbury; et al., "The Cytokine and Histological Response in Islet Xenograft Rejection is Dependent Upon Species Combination," Transplantation (1997), 64(9):1307-1314.

Metz; et al., "Application of proteomics in the discovery of candidate protein biomarkers in a diabetes autoantibody standardization program sample subset", J Proteome Res (Feb. 2008), 7(2):698-707.

Midha; et al., "Chemokine Expression in Nerve Allografts," Neurosurgery (2004), 54(6):1472-149.

O'Riordan; et al., "Bioinformatic Analysis of the Urine Proteome of Acute Allograft Rejection," Journal of American Society of Nephrology (2004), 15:3240-3248.

Roedder; et al., "The pits and pearls in translating operational tolerance biomarkers into clinical practice", Current Opinion in Organ Transplantation (Dec. 2012), 17(6):655-662.

Rotondi; et al. "High pretransplant serum levels of CXCL9 are associated with increased risk of acute rejection and graft failure in kidney graft recipients", Transpl Int (May 2010), 23(5):465-475.

Saint-Mezard; et al., "Analysis of independent microarray datasets of renal biopsies identifies a robust transcript signature of acute allograft rejection", Transplant International (Mar. 2009), 22(3):293-302.

Sarwal; et al., "Integrative Genomics to Identify Non-HLA Allogenic Kidney-Specific Targets after Kidney Transplantation", Transplantation (2008), 86(25):13, Oral Abstracts, downloaded Apr. 6, 2010.

Sarwal; et al., "Molecular Heterogeneity in Acute Renal Allograft Rejection Identified by DNA Microarray Profiling," New England Journal of Medicine (2003), 349(2):125-138.

Sato; et al. "Aberrant CD3- and CD3-mediated signaling events in cord blood T Cells are associated with dysfunctional regulation of Fas ligand-mediated cytotoxicity", The Journal of Immunology (Apr. 1999), 162 (8):4464-4471.

(56) References Cited

OTHER PUBLICATIONS

Scherer; et al., "Early Prognosis of the Development of Renal Chronic Allograft Rejection by Gene Expression Profiling of Human Protocol Biopsies", Transplantation (2003), 75(8):1323-30.
Serody; et al., "T-lymphocyte production of macrophage inflammatory protein-Ialpha is critical to the recruitment of CD8(+) T cells to the liver, lung, and spleen during graft-versus-host disease", Blood (2000), 96(9):2973-2980.
Shi; et al., "[Clinical significance of RANTES and MIP-1 alpha in acute rejection episode in kidney transplantation]", Zhongguo Yi Xue Ke Xue Yuan Xue Bao (2004), abstract.
Sigdel; et al. "Shotgun proteomics identifies proteins specific for acute renal transplant rejection", Proteomics Clin Appl (Jan. 2010), 4(1)32-47.
Sigdel; et al., "Profiling of autoantibodies in IgA nephropathy, an integrative antibiomics approach", Clin J Am Soc Nephrol (Dec. 2011), 6(12):2775-2784.
Simon; et al., "Serial Peripheral Blood Perforin and Granzyme B Gene Expression Measurements for Prediction of Acute Rejection in Kidney Graft Recipients," American Journal of Transplantation (2003), 3:1121-1127.
Teramoto; et al., "DNA Synthesis in Hepatocytes During Liver Allograft Rejection in Rats", Transplantation (1990), 50(2):199-201.
Thomson; et al., "Monitoring the Patient Off Immunosuppression" Transplantation (2001), 72(8):S13-S22.
Voshol; et al. "Evaluation of biomarker discovery approaches to detect protein biomarkers of acute renal allograft rejection", J Proteome Res (Jul.-Aug. 2005), 4(4):1192-1199.
Wakui; et al., "Genes Highly Expressed in the Early Phase of Murine Graft-Versus-Host Reaction," Biochemical and Biophysical Communications (2001), 282:200-206.
Whitfield; et al., "Systemic and Cell Type-Specific Gene Expression Patterns in Scleroderma Skin," Proc. Natl. Acad Sci. (2003), 100(21):12319-12324.
Wu, "Analysing Gene Expression Data From DNA Microarrays to Identify Candidate Genes," Journal of Pathology (2001), 195:53-65.
Zhang; et al., "Microarray Analysis of Gene Expression in Peripheral Blood Mononuclear Cells Derived From Long-Surviving Renal Recipients", Transplantation Proceedings (2002), 34:1757-1759.

"GeneChip 3' IVT Plus Reagent Kit", Affymetrix (2013), User Manual, 45 pgs.
"Affymetrix Human genome U133 Plus 2.0 Array", Gene Expression Omnibus (Nov. 2003), XP002627319, 3pgs.
Al-Lamki; et al., "Expression of Tumor Necrosis Factor Receptors in Normal Kidney and Rejecting Renal Transplants", Laboratory Investigation (Nov. 2001), 81(11): 1503-1515.
Chen; et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.
Hardiman, "Microarray platforms—comparisons and contrasts", Pharmacogenomics (Jan. 2004), 5(5): 487-502.
Hauser; et al., "Prediction of Acute Renal Allograft Rejection by Urinary Monokine Induced by IFN-gamma (MIG)", The American Society of Nephrology (Jan. 2005), 16(6):1849-1858.
Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.
Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8),1859-1867.
Morgun; et al., "Molecular Profiling Improves Diagnoses of Rejected and Infection in Transplanted Organs", Circulation Research (Jun. 2006), 98(12):e74-83.
Famulski; et al., "Changes in the Transcriptome in Allograft Rejection: IFN-γ-Induced Transcripts in Mouse Kidney Allografts", American Journal of Transplantation (Jun. 2006), 6(6):1342-1354.
Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.

* cited by examiner

| | Univariate | 95% CI (lower, upper) | p-value | multivariate | 95% CI | p-value |
|---|---|---|---|---|---|---|
| Weight | 0.28 | (-0.09, 0.41) | 0.2 | 0.155 | (-0.11, 0.42) | 0.23 |
| Mean SBP | 0.06 | (-0.41, 0.56) | 0.75 | -0.014 | (-0.55, 0.52) | 0.95 |
| Mean DBP | -0.04 | (-0.46, 0.38) | 0.85 | 0.016 | (-0.44, 0.47) | 0.93 |
| Hematocrit | 0.45 | (0.08, 2.85) | 0.03 | 0.558 | (-0.80, 1.92) | 0.387 |
| Initial GFR | 0.39 | (-0.01, 0.45) | 0.06 | 0.001 | (-0.25, 0.25) | 0.99 |
| 24hr proteinuria | -0.6 | (-5.89, -1.31) | 0.003 | -2.723 | (-5.04, -0.39) | 0.025 |
| PRKD1 | -0.58 | (-8.67, -1.82) | 0.004 | -4.738 | (-8.55, -0.91) | 0.019 |

CI: confidence interval, Univariate: Correlation coefficient (R), Multivariate: Regression coefficient, initial GFR (ml/min/1.73)

AUTOANTIBODY BIOMARKERS FOR IGA NEPHROPATHY

CROSS-REFERENCE TO RELATED APPLICATIONS

Pursuant to 35 U.S.C. §119 (e), this application claims priority to the filing date of U.S. Provisional Patent Application Ser. No. 61/472,408 filed on Apr. 6, 2011, the disclosure of which application is herein incorporated by reference.

INTRODUCTION

Immunoglobulin A (IgA) nephropathy (IgAN) is the most common primary glomerulonephritis in the world. It is diagnosed by evidence of mesangial deposits of IgA along with proliferation of mesangial cells on renal biopsy. It can lead to glomerular sclerosis and cause end-stage renal disease in 30-40% of affected patients within 20 years of disease onset. Though it is named for the deposition of IgA in the kidney, other types of immunoglobulins may also be involved. IgG and IgM deposits accompany IgA in some cases, with IgA deposits alone seen in approximately 15% of biopsies. Suzuki et al. (J. Clin. Invest. 2009; 119: 1668-1677) have highlighted the potential importance of IgG in the pathogenesis and progression of IgA nephropathy, as they found that highly specific IgG antibodies recognize aberrantly glycosylated IgA, and that these autoantibody levels correlated with disease activity, at least in terms of proteinuria, a powerful predictor of progression.

Accordingly, techniques for monitoring IgAN, including predicting, diagnosing and characterizing IgAN, are of interest. Autoantibody biomarkers to detect and track progression of IgA nephropathy are an unmet clinical need. The present invention meets these and other needs.

SUMMARY

Aspects of the invention include methods for diagnosing and monitoring IgAN in a subject. In embodiments of the methods, a sample from a subject is analyzed for the presence of one or more specific autoantibodies to determine the IgAN phenotype of the subject. Also provided are compositions, systems, kits and computer program products that find use in practicing embodiments of the methods described herein. The methods and compositions find use in a variety of different applications.

DEFINITIONS

Figure 1:
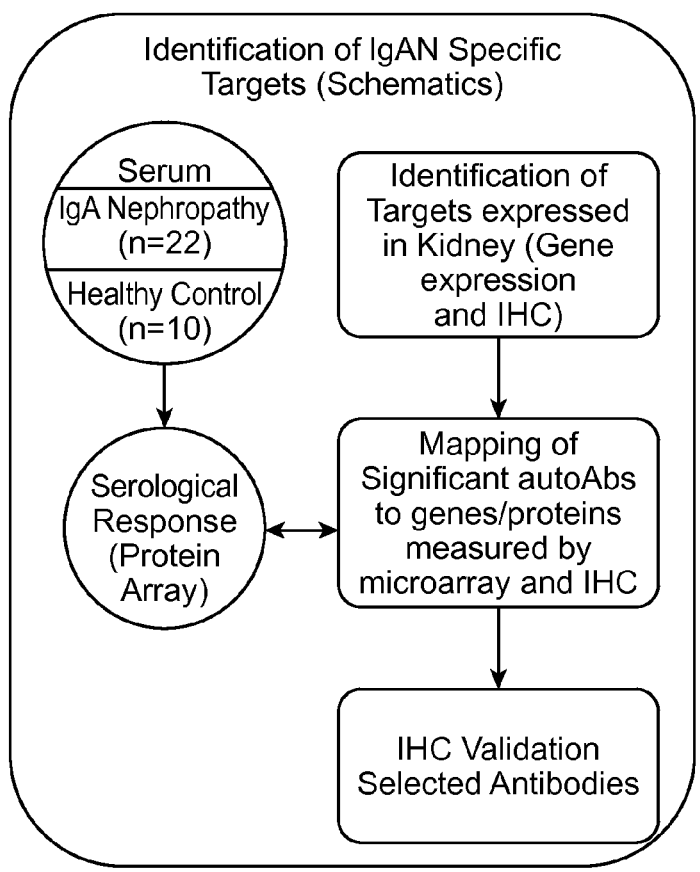
FIGS. 1A-E illustrate the method of identification of IgAN specific autoantibodies (autoAb) by immune response biomarker profiling. (A). Study flow diagram used to identify IgAN specific autoantibodies (autoAb) by immune response biomarker profiling, bioinformatics to map targets of significant autoAbs with genes and proteins expressed in kidney by microarray and IHC, and IHC validation. (B). A representative protein array from an IgAN patient in this study, probing approximately 8,200 proteins. (C). The biological functional classes of the proteins on the protoarray probed. (D). Quality control results from duplicate spots printed on the protoarray, demonstrating very stringent correlation ($R^2$=0.986). (E). A representative close up of the protoarray showing visible Alexa Fluorophore signal intensity differences in IgAN and healthy controls.
Figure 1:
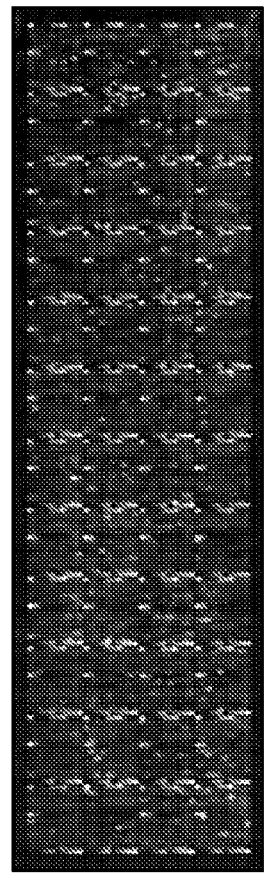
Figure 1:
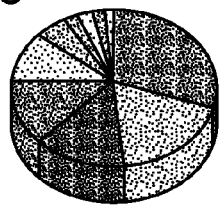
Figure 1:
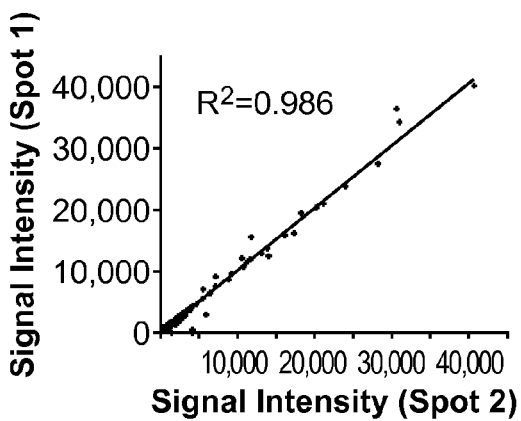
Figure 1:
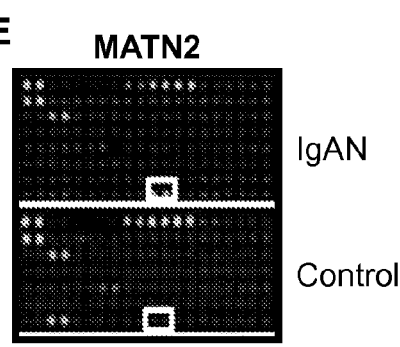

For convenience, certain terms employed in the specification, examples, and appended claims are collected here.

The term "autoantibody" as used herein refers to an antibody produced by an individual, where the antibody is directed against one or more 'self' antigens (e.g., antigens that are native to the individual, e.g., an antigen on a cell or tissue, or an endogenous peptide or protein).

The term "antibody signature" as used herein refers to the level of one or more antibodies, e.g., autoantibodies, in a sample. The level of an antibody in a sample (e.g., an autoantibody) may be qualitative or quantitative in nature.

The term "IgAN phenotype" as used herein refers to an observable characteristic or trait, or the absence thereof, relating to IgA Nephropathy (IgAN). In some cases, an IgAN phenotype may be used to determine that a subject has IgAN. For example, an IgAN phenotype may include increased levels of one or more autoantibodies in a subject, which indicates that the subject is experiencing IgAN, e.g., as compared to a control subject (i.e., one that is not experiencing IgAN). In some cases, an IgAN phenotype includes a non-IgAN phenotype (i.e., that the subject is not experiencing IgAN). Thus, an IgAN phenotype may include the absence of increased levels of one or more autoantibodies in a subject e.g., as compared to a control subject (i.e., one that is not experiencing IgAN). It is noted that comparisons to a positive control may also be used to determine an IgAN phenotype, e.g., comparing the autoantibody levels in a subject to a control subject with IgAN.

The terms "reference" and "control" are used interchangeably to refer to a known value or set of known values against which an observed value may be compared. As used herein, known means that the value represents an understood parameter, e.g., a level of expression of a marker gene in a graft survival or loss phenotype. A reference or control value may be from a single measurement or data point or may be a value calculated based on more than one measurement or data point (e.g., an average of many different measurements). Any convenient reference or control value(s) may be employed in practicing aspects of the subject invention.

The terms "protein", "polypeptide", "peptide" and the like refer to a polymer of amino acids (an amino acid sequence) and does not refer to a specific length of the molecule. This term also refers to or includes any modifications of the polypeptide (e.g., post-translational), such as glycosylations, acetylations, phosphorylations and the like. Included within the definition are, for example, polypeptides containing one or more analogs of an amino acid, polypeptides with substituted linkages, as well as other modifications known in the art, both naturally occurring and non-naturally occurring.

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" may include determining the amount of something present, as well as determining whether it is present or absent. In some instances, the term "determining" is used in connection with the evaluation of whether a subject has a condition of interest, e.g., a disease condition. In other words, the term determining may be used interchangeably with diagnosing. In such instances, the determination that is made is an ascertainment that the subject has the condition of interest based on data obtained as described herein, where the subject may or may not in fact have the condition of interest. Accordingly, methods of invention include methods which are not 100% accurate. Even though such determinations are not 100% accurate, they still provide useful information, e.g., in the context of making a decision that a subject is more likely than not to have a condition, is sufficiently likely to have a condition such that further a further evaluation (e.g., in the form of a second diagnostic test) or treatment regimen is warranted, etc. The terms "profile" and "signature" and "result" and "data", and the like, when used to describe antibody/protein/peptide level or gene expression level data are used interchangeably (e.g., antibody signature/profile/result/data, gene expression signature/profile/result/data, etc.).

DETAILED DESCRIPTION

Aspects of the invention include methods for diagnosing and monitoring IgAN in a subject. In embodiments of the methods, a sample from a subject is analyzed for the presence of one or more specific autoantibodies to determine the IgAN phenotype of the subject. Also provided are compositions, systems, kits and computer program products that find use in practicing embodiments of the methods described herein. The methods and compositions find use in a variety of different applications.

Aspects of the subject invention provide methods for diagnosing or monitoring IgAN in a subject. In certain embodiments, the methods include obtaining a sample from the subject (e.g., a blood or a urine sample) and determining the level of one or more autoantibodies therein to obtain an antibody signature of the sample. The antibody signature can then be used to determine the IgAN phenotype of the subject, e.g., by comparing to one or more antibody signatures from subjects known to not have IgAN. Such known antibody signatures can also be called controls or reference signatures/profiles. Also provided are compositions, systems, kits and computer program products that find use in practicing the subject methods.

Aspects of the subject invention include methods of diagnosing IgAN in a subject. Other aspects of the subject invention include methods of monitoring IgAN in a subject over time by determining and following changes in the antibody signatures of samples of the subject over time.

In certain embodiments the method includes: (a) evaluating the level of one or more autoantibodies in a sample from a subject to obtain an antibody signature; and (b) determining the IgAN phenotype of the subject based on the antibody signature. In certain embodiments, the antibody signature comprises autoantibody level data for one or more autoantibodies specific for proteins in one or more of the following categories: kidney specific antigens, e.g., glomerular proteins, tubular proteins, etc., proteins involved in apoptosis, proteins involved in cellular assembly and organization, proteins involved in cellular development, proteins involved in immunological disease, proteins involved in connective tissue disorders and proteins involved in dermatologica conditions (see Table 5 below). In certain embodiments, the autoantibodies are specific for proteins of Tables 1 and 2 (see below).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the subject invention provide methods for diagnosing and/or monitoring IgAN in a subject, as well as reagents, systems, kits and computer program products for use in practicing the subject methods. In further describing the invention, embodiments of the methods are described first in greater detail, followed by a review of embodiments of reagents, systems, kits and computer program products for use in practicing embodiments of the methods.

Methods for Diagnosing and Monitoring IgA Nephropathy

As summarized above, methods for diagnosing and/or monitoring IgAN in a subject are provided. In certain embodiments, the methods can be considered methods of diagnosing IgAN in a subject. In certain embodiments, the method can be considered a method of monitoring IgAN in a subject to determine the progression of the disease, e.g., at one or more time points after diagnosis of IgAN. The diagnosis and monitoring of IgAN can be performed by determining the IgAN phenotype of the subject using the methods of the subject invention. In certain embodiments, the subject methods distinguish a particular IgAN phenotype in a subject from other IgAN categories, including chronic IgAN, acute IgAN, rapidly-progressive IgAN, or a secondary IgAN such as Henoch-Schonlein purpura (HSP), etc.

In practicing embodiments of the methods, the sample (e.g., serum or urine sample) is assayed to obtain an antibody signature of the sample, or protein profile, in which the amount of one or more autoantibodies specific to antigens (e.g., peptides/proteins) in the sample is determined, where the determined amount may be qualitative and/or quantitative in nature. In certain embodiments, the antibody signature includes measurements for the amount of one or more autoantibodies specific for proteins (or peptides derived therefrom) shown in Tables 1 and 2.

TABLE 1

| Gene symbol | Gene name |
| --- | --- |
| PRKD1 | Serine/threonine-protein kinase D1 |
| MATN2 | Matrilin-2 |
| DDX17 | DEAD (Asp-Glu-Ala-Asp) box polypeptide 17 2 |
| UBE2W | ubiquitin-conjugating enzyme E2W |

TABLE 1-continued

| Gene symbol | Gene name |
| --- | --- |
| CDKN1B | cyclin-dependent kinase inhibitor 1B |
| SOD2 | superoxide dismutase 2, mitochondrial |
| IQCK | IQ motif containing K |
| BLZF1 | basic leucine zipper nuclear factor 1 |
| EFNA3 | ephrin-A3 |
| EIF4A2 | eukaryotic translation initiation factor 4A |
| FLII | flightless I homolog |
| LIMCH1 | LIM and calponin homology domains 1 |
| MAGA4 | melanoma antigen family A, 4 |
| MEF2D | myocyte enhancer factor 2D |
| MLLT6 | myeloid/lymphoid or mixed-lineage leukemia (trithorax homolog, Drosophila); translocated |
| CIAPIN/CIAPIN1 | cytokine induced apoptosis inhibitor 1 |
| GDI2 | GDP dissociation inhibitor 2 |
| HSPA8 | heat shock 70 kDa protein 8, transcript variant |
| SERPINA5 | serpin peptidase inhibitor, clade A (alpha-1 antiproteinase, antitrypsin), member 5 |
| TGM1 | transglutaminase 1 (K polypeptide epidermal type I, protein-glutamine-gamm a-glutamyltransferase) |

TABLE 2

| Gene symbol | Gene name |
| --- | --- |
| FLOT2 | flotillin 2 |
| BRD9 | bromodomain containing 9 |
| CDS2 | CDP-diacylglycerol synthase (phosphatidate cytidylyltransferase) 2 |
| MRPL28 | mitochondrial ribosomal protein L28 |
| MUTED | muted homolog |
| NKAIN4 | Na+/K+ transporting ATPase interacting 4 |
| PCTK1 | PCTAIRE protein kinase 1 |
| PLXNA1 | plexin A1 |
| PODN | podocan |
| POLH | polymerase (DNA directed), eta |
| PRKD2 | protein kinase D2 |
| RNF113A | ring finger protein 113A |
| SEPT5 | septin 5 |
| TNS1 | tensin 1 |
| TOM1 | target of myb1 |
| TRPV4 | transient receptor potential cation channel, subfamily V, member 4 |
| USP12 | ubiquitin specific peptidase 12 |
| ZMYM3 | zinc finger, MYM-type 3 |

As detailed in the Examples section below, protein analysis identified antibody signatures with predictive power for clinical transplant categories. The term antibody signature or antibody profile is used broadly to include a profile of one or more different autoantibodies specific for antigens in the sample. In certain embodiments, the target antigens are derived from expression products of one or more genes. In certain embodiments, the level of only one autoantibody specific for a protein shown in Tables 1 and 2 is evaluated. In yet other embodiments, the level of two or more autoantibodies specific for proteins from Tables 1 and 2 are evaluated, e.g., 3 or more, 4 or more, 5 or more, 6 or more, 7 or more, 8 or more, 9 or more, 10 or more, 15 or more, or 20 or more, etc. It is noted that the level of one or more additional antibodies specific for antigens other than those listed in Tables 1 and 2 can also be evaluated in the antibody signature.

In the broadest sense, autoantibody level evaluation may be qualitative or quantitative. As such, where detection is qualitative, the methods provide a reading or evaluation, e.g., assessment, of whether or not the target analyte (e.g., autoantibody) is present in the sample being assayed. In yet other embodiments, the methods provide a quantitative detection of the target analyte in the sample being assayed, i.e., an evaluation or assessment of the actual amount or relative abundance of the target analyte, e.g., an autoantibody in the sample being assayed. In such embodiments, the quantitative detection may be absolute or, if the method is a method of detecting two or more different analytes in a sample, relative. As such, the term "quantifying" when used in the context of quantifying a target analyte in a sample can refer to absolute or to relative quantification. Absolute quantification may be accomplished by inclusion of known concentration(s) of one or more control analytes and referencing the detected level of the target analyte(s) with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other. In addition, a relative quantitation may be ascertained using a control, or reference, value (or profile) from one or more control sample. Control/reference profiles are described in more detail below.

In some embodiments, the invention provides methods for determining whether a patient or subject has an IgAN phenotype with a high positive predictive value (PPV). The term "PPV" is used in its art accepted manner and defined as True Positives (TP)/(TP+False Positives (FP)), In some instances, the determination that is made has a PPV that 60, 70, 80, 90, 95, or 99.9% or higher. In some embodiments, the invention provides methods for determining whether a patient or subject has an IgAN phenotype, wherein the PPV is equal or higher than 80%. In some embodiments, the invention provides methods for determining whether a patient or subject has an IgAN phenotype, wherein the negative predictive value (NPV) is 60, 70, 80, 90, 95, or 99.9% or higher. The term "NPV" is used in its art accepted manner and is defined as True Negatives (TN)/(TN+False Negatives (FN)). In some embodiments, the invention provides methods for determining whether a patient or subject has an IgAN phenotype, wherein the NPV is higher than 80%.

In some embodiments, the invention provides methods for determining whether a patient or subject has an IgAN phenotype with a high specificity. The term "specificity" is used in its art accepted manner and is defined as TN/(TN+FP). In some instances, the specificity is 60, 70, 80, 90, 95, or 99.9% or higher. In some embodiments, the invention provides methods for determining whether a patient or subject has an IgAN phenotype, wherein the specificity is equal or higher than 80%.

In some embodiments, the invention provides methods for determining whether a patient or subject has an IgAN phenotype with a high sensitivity. The term "sensitivity" is used in its art accepted manner and is defined as TP/(TP+FN). In some instances, the sensitivity of the methods is 60, 70, 80, 90, 95, or 99.9% or higher. In some embodiments, the invention provides methods for determining whether a patient or subject has an IgAN phenotype wherein the sensitivity is higher than 80%.

In some embodiments, the invention provides methods for determining whether a patient or subject has an IgAN phenotype, wherein the Area Under the Curve (AUC) value is 0.5, 0.6, 07, 0.8 or 0.9 or higher. The term "AUC" is used in its art accepted manner and is defined as the area under the Receiver Operating Characteristic (ROC) curve. The ROC curve is used in its art accepted manner and is defined as a plot of test sensitivity (True Positive Rate: TPR) versus (1-specificity) (False Positive Rate: FPR). In some embodiments, the invention provides methods for determining whether a patient or subject has an IgAN phenotype, wherein the AUC value is 0.7 or higher. In some embodiments, the invention provides methods for determining whether a patient or subject has an IgAN phenotype, wherein the AUC value is 0.8 or higher. In some embodiments, the invention provides methods for determining whether a patient or subject has an IgAN phenotype, wherein the AUC value is 0.9 or higher.

In some embodiments, the p value in the analysis of the methods described herein is 0.05, 04, 0.03, 0.02, 0.01, 0.009, 0.005, or 0.001 or below. In some embodiments, the p value is 0.001 or below. Thus in some embodiments, the invention provides methods for determining whether a patient or subject has an IgAN phenotype, wherein the p value is 0.05, 04, 0.03, 0.02, 0.01, 0.009, 0.005, or 0.001 or below. In some embodiments, the p value is 0.001 or below.

In certain embodiments, additional analytes beyond those listed above may be assayed, where the additional analytes may be additional proteins (e.g., antibodies, autoantibodies), additional nucleic acids, or other analytes. For example, genes whose expression level/pattern is modulated during the progression of IgAN can be evaluated (e.g., from a biopsy sample, blood sample, urine sample, etc., from the subject). In certain embodiments, additional analytes may be used to evaluate additional characteristics, including but not limited to: serum proteins in urine to correlate with proteinuria; age or body mass index associated genes that correlate with renal pathology; immune tolerance markers; genes found in literature surveys with immune modulatory roles, etc. In addition, other function-related analytes may be evaluated, e.g., for assessing sample quality, sampling error (e.g., in biopsy-based studies), and normalizing antibodies for calibrating results.

The antibody signature of a sample can be obtained using any convenient method for antibody or protein/peptide analysis. As such, no limitation in this regard is intended. Exemplary peptide analysis includes, but is not limited to: HPLC, mass spectrometry, LC-MS based peptide profiling (e.g., LC-MALDI), Multiple Reaction Monitoring (MRM), ELISA, protein microarray profiling, and the like.

In practicing the methods of the present invention, any convenient protein evaluation/quantitation protocol may be employed, where the levels of one or more antibodies in the assayed sample are determined to generate an antibody signature for the sample. Representative methods include, but are not limited to: MRM analysis, standard immunoassays (e.g., ELISA assays, Western blots, FACS based protein analysis, etc.), multiplex protein assays (e.g., protein microarray assays), protein activity assays, etc. For example, autoantibody levels may be determined by readily adapting methods that are described by Robinson et al. ("Protein arrays for autoantibody profiling and fine-specificity mapping." Proteomics 2003, 3, 2077-2084), the disclosure of which is incorporated by reference in its entirety.

In some instances, protein arrays/microarrays are employed. The terms "array" and "microarray" are used interchangeably herein. A protein array may include one or more known polypeptides (antigens) immobilized at known locations on a solid support. The arrayed polypeptides are potentially capable of capturing an antibody from the subject sample. A protein array may include 10 or more, 25 or more, 50 or more, 100 or more, or 1000 or more, including 5000 or more, 10,000 or more, or 20,000 or more different proteins. A protein array employed in methods of the invention can be constructed anew or may be commercially available, e.g. ProtoArray® Human Protein Microarrays (Invitrogen).

In practicing certain embodiments the methods where arrays are employed, once the array is contacted with a sample, the antibodies from the sample bind to their respective target antigens on the protein array. The array may be subjected to one or more washes as desired, e.g., to remove excess sample, including unbound constituents. Next, a detection step is employed. Detection methods depend on how the samples were prepared prior to contact with the array, but may, for example, include direct or indirect immunofluorescence, as well as colorimetric techniques based on silver-precipitation, chemiluminescence, label free Surface Plasmon Resonance, etc. In some instances, detection may include indirect immunofluorescence, in which the array, following the wash steps described above, is contacted with a secondary antibody (directed against the species from which the sample was derived, e.g. anti-human) that is conjugated to a fluorescent molecule, i.e. a fluorophore, The array is then scanned, using any one of a number of microarray scanners that are standard in the art, to produce an image. The spots on the resulting image can be quantified by commonly used microarray quantification software packages. The resulting location and intensity of each spot can be used to determine the identity and quantity of the antibodies (autoantibodies) that were present in the original sample. Thus, a protein array may be employed to provide the antibody signature from a subject.

Following obtainment of the antibody signature from a subject, the antibody signature is analyzed/evaluated to determine the IgAN phenotype of the subject (e.g., whether or not the subject has IgAN or a progression of IgAN over time). In certain embodiments, analysis includes comparing the antibody signature with a reference or control signature, e.g., a reference or control; antibody signature, to determine the IgAN phenotype of the subject. The terms "reference" and "control" as used herein mean a standardized analyte level (or pattern) that can be used to interpret the analyte pattern of a sample from a subject. For example, a reference profile can include antibody or target protein level data relating to one or more antibodies of interest being evaluated in the sample of the subject/patient. The reference or control profile may be a profile that is obtained from a subject (a control subject) having a IgAN phenotype, and therefore may be a positive reference or control signature for IgAN. In addition, the reference/control profile may be from a control subject known not to have IgAN, and therefore be a negative reference/control signature. In some embodiments, the IgAN phenotype is determined by comparison of the subject's antibody profile to a positive control profile. Such IgAN phenotypes may indicate that the subject does not have IgAN.

In certain embodiments, the obtained antibody signature is compared to a single reference/control profile to determine the subject's IgAN phenotype. In yet other embodiments, the obtained antibody signature is compared to two or more different reference/control profiles to obtain additional or more in depth information regarding the IgAN phenotype of the subject. For example, the obtained antibody signature may be compared to a positive and negative reference profile to obtain confirmed information regarding the progression or type of IgAN in the subject.

The comparison of the obtained antibody signature and the one or more reference/control profiles may be performed using any convenient methodology, where a variety of methodologies are known to those of skill in the array art, e.g., by comparing digital images of the antibody/protein signatures by comparing databases of peptide signatures and/or gene expression profiles, etc. Patents describing ways of comparing expression profiles include, but are not limited to, U.S. Pat. Nos. 6,308,170 and 6,228,575, the disclosures of which are herein incorporated by reference, and may be readily adapted for use in the subject methods.

The comparison step results in information regarding how similar or dissimilar the obtained antibody signature is to the control/reference profile(s), which similarity/dissimilarity information is employed to determine the IgAN phenotype of the subject. For example, similarity of the obtained antibody signature with the antibody signature of a control sample from a subject experiencing IgAN indicates that the subject is experiencing IgAN. Likewise, similarity of the obtained antibody signature with the antibody signature of a control sample from a subject that has not had (or isn't experiencing) IgAN indicates that the subject is not experiencing IgAN.

Depending on the type and nature of the reference/control profile(s) to which the obtained antibody signature is compared, the above comparison step yields a variety of different types of information regarding the subject as well as the sample employed for the assay. As such, the above comparison step can yield a positive/negative determination of an ongoing IgAN condition. In certain embodiments, the determination/prediction of IgAN can be coupled with a determination of additional characteristics, such as glomerular filtration rate (GFR) and urine protein measurement (e.g. for proteinuria).

In certain embodiments, a reference profile is a composite reference profile, having control data derived from more than one subject and/or sample. For example, a reference profile may include average autoantibody level data from samples of subjects having experienced the same or similar progression of IgAN.

The subject methods further find use in pharmacological applications. In these applications, a subject/host/patient is first diagnosed with IgAN according to the subject invention, and then treated using a protocol determined, at least in part, on the results of monitoring the IgAN in the subject. For example, a subject may be evaluated for the presence or absence of IgAN using a protocol such as the diagnostic protocol described above. If IgAN is present, the subject may be monitored using a method described herein. The subject may then be treated using a protocol whose suitability is determined using the results of the diagnosing and/or monitoring steps. For example, where the subject is categorized as having a IgAN phenotype, therapy can be modulated, e.g., increased or drugs changed, as is known in the art for the treatment/prevention of IgAN.

In practicing such monitoring methods, a subject is typically tested/screened for IgAN following receipt of treatment for the same. The subject may be screened once or serially following treatment, e.g., weekly, monthly, bimonthly, half-yearly, yearly, etc. In certain embodiments, the subject is monitored prior to the occurrence of IgAN. In certain other embodiments, the subject is monitored following the occurrence of IgAN.

The subject methods may be employed with a variety of different types of subjects. In many embodiments, the subjects are within the class mammalian, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the animals or hosts, i.e., subjects (also referred to herein as patients) are humans.

In practicing the subject methods, a subject or patient sample, e.g., cells or collections thereof, e.g., tissues, fluids, etc., e.g., urine or serum, is assayed to determine the IgAN phenotype of the host from which the assayed sample was obtained. Accordingly, the subject methods include obtaining a suitable sample from the subject or patient of interest. The sample is derived from any initial suitable source, where sample sources of interest include, but are not limited to, many different physiological sources, e.g., cerebrospinal fluid (CSF), urine, saliva, serum, tears, tissue derived samples, e.g., homogenates, and blood or derivatives thereof.

In certain embodiments, a suitable initial source for the patient sample is serum. As such, the sample employed in the subject assays of these embodiments is generally a serum fraction. The blood derived sample may be derived from whole blood or a fraction thereof, e.g., serum, plasma, etc.

Any suitable protocol for obtaining such samples may be employed. Moreover, in certain embodiments, samples may be obtained from a third party (e.g., a sample may be obtained from a third party that independently collects the sample from a subject).

Aspects of the present invention include methods of diagnosing or monitoring IgAN in a subject by evaluating the level of one or more autoantibodies in a sample (e.g., a blood or urine sample) from the subject to obtain an antibody signature and determining the IgAN phenotype of the subject based on the antibody signature. In certain embodiments, the one or more autoantibodies include at least one antibody specific for a protein of Table 1. In certain embodiments, the one or more autoantibodies include at least one antibody specific for a protein of Table 2. In certain embodiments, the one or more autoantibodies include at least one antibody specific for a protein selected from PRKD1, MATN2, DDX17, UBE2W, CDKN1B, SOD2, FLOT2, IQCK, BLZF1, BRD9, CDS2, EFNA3, EIF4A2, FLII, LIMCH1, MAGEA4, MEF2D, MLLT6, MRPL28, MUTED, NKAIN4, PCTK1, PLXNA1, PODN, POLH, PRKD2, RNF113A, SEPT5, TNS1, TOM1, TRPV4, USP12, ZMYM3, CIAPIN1, GDI2, HSPA8, SERPINA5 and TGM1. As such, the antibody signature may contain autoantibody level data for one autoantibody, 2 or more autoantibodies, 3 or more autoantibodies, 4 or more autoantibodies, 5 or more autoantibodies, 6 or more autoantibodies, 7 or more autoantibodies, 8 or more autoantibodies, 9 or more autoantibodies, 10 or more autoantibodies, 15 or more autoantibodies, or 20 or more autoantibodies, etc., specific for proteins that are described herein. The selection of which autoantibodies specific for proteins from Tables 1 and 2 that are to be included in the antibody signature will be determined by the desires of the user. No limitation in this regard is intended.

Table 1 shows a list of 20 proteins. Assaying for autoantibodies specific for one or more of the proteins in Table 1 in a subject can be used to determine an IgAN phenotype of the subject. The levels of autoantibodies specific for one or more of these 20 proteins is significantly higher in a IgAN phenotype with respect to a normal control (e.g., one or more autoantibodies described herein are at significantly higher levels in a subject exhibiting IgAN as compared to a normal control, i.e., a subject not having IgAN).

In certain embodiments, the one or more autoantibodies in the antibody signature includes autoantibodies specific for the proteins MATN2, UBE2W, DDX17 and PRKD1. In such embodiments, the subject is determined to have IgAN when the level of autoantibodies specific for one or more of these proteins in the sample is increased as compared to a control reference antibody signature.

In certain embodiments, the one or more autoantibodies in the antibody signature includes an autoantibody specific for the protein PRKD1. In such embodiments, the subject is determined to have IgAN when the level of the autoantibody to PRKD1 in the sample is increased as compared to a control reference antibody signature.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to autoantibodies specific for proteins that find use as markers for diagnosing or monitoring IgAN are specifically embraced by the present invention and are disclosed herein just as if each and every combination was individually and explicitly disclosed. As such, any combination of autoantibodies specific for proteins from Tables 1 and 2 are disclosed herein just as if each and every such sub-combination of proteins was individually and explicitly disclosed herein.

Databases of Profiles of Phenotype Determinative Genes

Also provided are databases of antibody signatures of different IgAN phenotypes. The antibody signatures and databases thereof may be provided in a variety of media to facilitate their use (e.g., in a user-accessible/readable format). "Media" refers to a manufacture that contains the expression profile information of the present invention. The databases of the present invention can be recorded on computer readable media, e.g. any permanent medium (not a carrier wave) that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user via a graphical user interface. One format for an output means ranks protein profiles (e.g., an antibody signature) possessing varying degrees of similarity to a reference protein profile (e.g., a reference antibody signature). Such presentation provides a skilled artisan (or user) with a ranking of similarities and identifies the degree of similarity contained in the test profile to one or more references profile(s). Embodiments of the subject systems include the following components: (a) a communications module for facilitating information transfer between the system and one or more users, e.g., via a graphical user interface; and (b) a processing module for performing one or more tasks involved in the analysis methods of the invention.

As such, the subject invention further includes a computer program product for determining a IgAN phenotype of a subject. The computer program product, when loaded onto a computer, is configured to employ a antibody signature from a sample from a subject to determine a IgAN phenotype for the subject. Once determined, the IgAN phenotype can be provided to a user in a user-readable format. In certain embodiments, the antibody signature includes data for the level of one or more autoantibodies specific for proteins listed in Tables 1 and 2. In addition, the computer program product may include one or more reference or control antibody signatures (as described in detail above) which are employed to determine the clinical transplant category of the patient.

Thus, aspects of the present invention include computer program products for determining whether a subject is experiencing IgAN. The computer program product, when loaded onto a computer, is configured to employ an antibody signature from a sample from the subject to determine whether the subject has IgAN, and provide the determined IgAN result to a user in a user-readable format, wherein the antibody signature comprises data for the level of one or more autoantibodies specific for proteins listed in Tables 1 and 2.

Reagents, Systems and Kits

Also provided are reagents, systems and kits thereof for practicing one or more of the above-described methods. The subject reagents, systems and kits thereof may vary greatly. Reagents of interest include reagents specifically designed for use in production of the above-described antibody signatures. These include a protein level evaluation element made up of one or more reagents. The term system refers to a collection of reagents, however compiled, e.g., by purchasing the collection of reagents from the same or different sources. The term kit refers to a collection of reagents provided, e.g., sold together.

The subject systems and kits include reagents for peptide or protein (e.g., autoantibody) level determination, for example those that find use in ELISA assays, Western blot assays, MS assays (e.g., LC-MS), HPLC assays, flow cytometry assays, array based assays, and the like. One type of such reagent is one or more probe specific for one or more autoantibodies specific for proteins listed in Tables 1 and 2. For example, the target proteins of Tables 1 and 2 or fragments thereof (as are well known in the art) find use in the subject systems as probes. In certain embodiments, protein arrays containing target proteins at known locations on a substrate are provided in the subject systems (see, e.g., U.S. Pat. Nos. 4,591,570; 5,143,854; 7,354,721; the disclosures of which are herein incorporated by reference, and may be readily adapted for use in the subject invention). Probes for any combination of autoantibodies described herein may be employed. The subject arrays may include probes for one or more autoantibodies to only those proteins that are listed in Tables 1 and 2 or may include additional probes that are not listed therein, such as probes for proteins whose level can be used to evaluate additional characteristics as well as other array assay function related proteins, e.g., for assessing sample quality, sampling error, and normalizing protein levels for calibrating results, and the like.

The systems and kits of the subject invention may include the above-described arrays and/or specific probes or probe collections. The systems and kits may further include one or more additional reagents employed in the various methods, such as various buffer mediums, e.g. incubation and washing buffers, prefabricated probe arrays, labeled probe purification reagents and components, like spin columns, etc., signal generation and detection reagents, e.g. secondary antibodies (e.g., conjugated to detectable moieties, e.g., horseradish peroxidase (HRP), alkaline phosphatase, etc.), chemifluorescent or chemiluminescent substrates, fluorescent moieties, and the like.

The subject systems and kits may also include a phenotype determination element, which element is, in many embodiments, a reference or control protein/peptide (e.g., autoantibody) signature or gene expression profile that can be employed, e.g., by a suitable computing means, to determine a IgAN phenotype based on an "input" antibody signature. Representative phenotype determination elements include databases of antibody signatures, e.g., reference or control profiles, as described above.

In addition to the above components, the subject systems/kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the Internet to access the information at a removed site. Any convenient means may be present in the kits.

Aspects of the present invention thus provide systems for diagnosing and monitoring IgAN in a subject. The system includes: an antibody level evaluation element configured for evaluating the level of one or more autoantibodies in a sample from a subject to obtain an antibody signature, where the one or more autoantibodies includes an autoantibody specific for a protein of Tables 1 and/or 2; and a phenotype determination element configured for employing the antibody signature to determine the IgAN phenotype of the subject.

In certain embodiments, the one or more autoantibodies in the antibody signature includes autoantibodies to the proteins MATN2, UBE2W, DDX17 and PRKD1. In certain embodiments, the one or more autoantibodies in the antibody signature include an autoantibody specific for the protein PRKD1.

The following examples are offered by way of illustration and not by way of limitation.

EXPERIMENTAL

Methods

Summary

High-density protein microarrays evaluated IgG autoantibodies (autoAbs) in the serum of IgAN patients (n=22) and controls (n=10). Clinical parameters, including annual Glomerular filtration rate (GFR) and urine protein measurements were collected on all patients over 5 years. Bioinformatic data analysis was performed to select targets for further validation by immunohistochemistry (IHC).

Patients

Thirty two subjects from Stanford University Medical Center participated in this study including 22 patients with biopsy confirmed IgAN and 10 age and gender matched healthy controls (HC). IgAN subjects were divided into two groups based on their rate of decline of measured GFR over the 5 year follow-up. Patients were labeled as progressors (IgAp; n=7) if their rate of measured GFR decline was more than 5.0 mL/min/year. IgAN patients with a delta GFR of less than 5.0 mL/min/year were labeled non-progressors (IgAnp).

The demographics of all 22 IgAN patients are provided in Table 3. The IgAN patients underwent annual clearance studies over a 5 year follow-up, with the exception of those who had progressed to end-stage renal failure. GFR was examined using the urinary clearance of inulin, as previously described (Squarer et al. "Mechanisms of progressive glomerular injury in membranous nephropathy." J. Am. Soc. Nephrol. 1998; 9: 1389-1398). Blood (5 mL serum) and urine (50 mL) samples were collected annually over 4-5 years from each IgAN patient. 17 patients with non-IgAN glomerular disease (9 focal glomerulosclerosis (FSGS) and 8 membranous nephropathy) were chosen for a comparison with IgAN autoAbs profiling. AutoAbs elevated in non-IgAN glomerular disease were based on the comparison with AutoAbs levels from 12 healthy controls.

TABLE 3

Patient Demographics 3a (IgAN vs healthy control)

| | IgAN* | Healthy Control* | P-value** |
|---|---|---|---|
| Age (yr) | 38.0 ± 10.2 | 29.9 ± 10.4 | 0.05 |
| Gender (M/F) | 12/10 | 5/5 | 0.82 |
| Ht (cm) | 170.0 ± 11.3 | 169.4 ± 10.2 | 0.85 |
| Mean SBP (mmHG) | 131.5 ± 9.8 | 117.1 ± 1 | 0.03 |
| Mean DBP(mmHG) | 79.0 ± 13.2 | 73.6 ± 5.9 | 0.16 |
| Serum Cr (mg/dL) | 1.0 ± 0.31 | 0.94 ± 0.18 | 0.02 |
| GFR (mL/min/1.73) | 72.0 ± 21.72 | 108.2 ± 12.6 | 2.2E−06 |
| Delta GFR (mL/min/yr) | −5.0 ± 12.04 | Na | na |
| Proteinuria (g/d) | 2.o ± 2.05 | Nd | na |

3b (Progressors vs Non-progressors)

| | Progressor* | Non-Progressor* | P-value** |
|---|---|---|---|
| Age (yr) | 39.7 ± 7.3 | 37.6 ± 11.5 | 0.67 |
| Gender (M/F) | 5/2 | 7/8 | 0.30 |
| Ht (cm) | 176.5 ± 8.9 | 168 ± 12.2 | 0.26 |
| Mean SBP (mmHG) | 131.5 ± 9.8 | 130.3 ± 12.4 | 0.82 |
| Mean DBP (mmHG) | 82.2 ± 9.14 | 77.98 ± 14.8 | 0.49 |
| Serum Cr (mg/dL) | 1.38 ± 0.22 | 1.05 ± 0.28 | 0.01 |
| GFR (mL/min/1.73) | 57 ± 13.7 | 79 ± 21.4 | 0.02 |
| Delta GFR (mL/min/yr) | −16.4 ± 15.3 | 0.19 ± 4.78 | 0.0009 |
| Proteinuria (g/dL) | 3.87 ± 2.63 | 1.28 ± 0.93 | 0.04 |

*Values are presented in mean ± SD.
**P values are calculated to evaluate whether there is any significant difference between the two groups Measurement of IgG and IgA Levels in the Serum To control for differences in the level of immunoglobulins in IgAN patients, human IgG ELISA (Cat #E-80G) and Human IgA ELISA (Cat #E-80A) kits (Immunology Consultants Laboratory, Inc. Newberg, Oreg.) were used to measure total IgG and IgA in the sera. After 1:80,000 dilution, ELISA analysis was done following standard protocols (Sigdel et al. "Novel Shotgun Proteomics Approach Identifies Proteins Specific for Acute Renal Transplant Rejection." Am. J. Transplantation 2010; 10: 289-290). Protein concentration was determined from the generated standard curve.

Immune Response Profiling Using Protein Microarrays

ProtoArray® Human Protein Microarray v4.0 (Invitrogen, Carlsbad, Calif.) was used to characterize the specificity of IgG specific autoAb responses in IgAN. The arrays contain approximately 8000 recombinant human proteins expressed as N-terminal GST fusion proteins and spotted on the nitrocellulose-coated glass slide (FIG. 1B). Established protocols (Invitrogen), (Li et al. "Identifying compartment-specific non-HLA targets after renal transplantation by integrating transcriptome and "antibodyome" measures." Proc. Natl. Acad. Sci. USA 2009; 106: 4148-4153) were followed for serum sample preparation, blocking, probing, drying, scanning, and data acquisition. At the end of the washing the slides were dried by centrifugation and scanned using Axon GenePix 4000B Scanner (Molecular Devices. Sunnyvale, Calif.). Raw signal intensity data was acquired using GenePix pro 6.0 software (Molecular devices, Sunnyvale, Calif.) and initial data acquisition was done using ProtoArray® Prospector 5.2. The detailed method is described elsewhere (Li et al., ibid; Sutherland et al. "Protein microarrays identify antibodies specific for protein kinase C-zeta that are associated with a greater risk of allograft loss in pediatric renal transplant recipients." Kidney Int. 2009; 76: 1277-1283).

Protein Array Data Processing and Analysis

The relative fluorescence intensity (RFU) was measured using GenePix pro 6.0 (Molecular Devices, Sunnyvale, Calif.) and initial data processing was done using ProtoArray® Prospector 5.2. Fluorescent signal values were measured for each protein after adjusting for background correction so that Z-factors for all the corrected intensities of the human protein features could be calculated. Differentially increased Ab signal in IgAN was analysed after Linear Model Normalization using the Robust Linear Model (Sboner et al. "Robust-linear-model normalization to reduce technical variability in functional protein microarrays." J. Proteome Res. 2009; 8: 5451-5464). Based on our previous quality control experience (Li et al., ibid; Sutherland et al. ibid), the minimal signal threshold was set at 500 relative fluorescence units (RFU) and signal difference required between IgAN and HC for any Ab was at least 200 RFU, and a Z-Score value of >3.0 was used as a parameter to identify significant Ab signal. The platform is developed in such a way that it normalizes the concentration variability in IgG level in the serum using IgG gradients and other internal controls printed on arrays. Pearson correlation coefficients between selected antibodies and the rate of renal function decline (delta inulin GFR, mL/yr) were calculated after transforming Ab signal intensities with the use of base-2 logarithms. The list of AutoAbs highly expressed in both IgAN and non-IgAN group were cross-mapped based on statistical significance (P value<0.05).

The analysis was also done with SAS software (version 9.2, enterprise guide 4.2). The pathway analysis was performed using Ingenuity Pathway Analysis (IPA) (Ingenuity, Redwood City, Calif.). Hypergeometric distribution was used to assess whether the proportion of 99 non-immunoglobulin targets expressed in kidney was significant.

Immunohistochemistry (IHC)

Tissue specific expression by Immunohistochemical staining was performed on formalin fixed paraffin embedded biopsy tissue to evaluate the presence of PRKD1, UBE2W, and IGKC using corresponding antibodies. IHC of these antigens was tested on a new set of 5 IgAN kidney biopsy samples and 5 new normal kidney control samples obtained from the normal kidney region obtained from nephrectomy samples for renal tumor.

Protein G purified rabbit anti-human PRKD1 polyclonal antibody (LIFESPAN BIOSCIENCES, Seattle, Wash., Cat #LS-C98928), Protein G purified mouse anti-human UBE2W monoclonal antibody (Abcam Inc., Cambridge, Mass., Catalog #ab55034), and Goat anti-human kappa light chain (IGKC) polyclonal antibody (Abcam Inc., Cambridge, Mass., Catalog #ab55034) were used for this purpose. The paraffin sections were dewaxed and hydrated to deionized water, followed by citrate buffer pH6 antigen retrieval with a Biocare Medical pressure cooker (or Biocare Medical Decloaking Chamber). All the sections were blocked with 3% hydrogen peroxide for 8 minutes and then normal serum 20 to 30 minutes prior to incubation with the antibodies. The slides were then incubated for 30 minutes with the specific antibodies (UBE2W 1:50 and IGKC 1:100) at room temperature. Subsequently, the slides were rinsed for 3 min in PBS (pH 7.4) 3 times and incubated with the Dako EnVion+Peroxidase system for 30 minutes as well as with the appropriate secondary antibody. The peroxidase catalyzed product was visualized with Dake DAB chromogen. The sections were then lightly counterstained with hematoxylin for 1 min, rinsed, intensified, dehydrated and mounted for quantitative analysis.

Results

Summary 117 (1.4%) specific antibodies were increased in IgAN. Amongst these antibodies were autoAb to immunoglobulin family proteins. IgAN specific autoAb (~50%) were mounted against proteins predominantly expressed in glomeruli and tubules, selected candidates were verified by IHC. Correlation analysis identified that patients with disease progression have increased autoAb to PRKD1, a member of the protein kinase C (PKC) family, also highly expressed in the kidney.

IgG and IgA Levels in IgAN Patients

Commercially available ELISA was used to measure total IgA level in the sera. As expected, the IgA levels were found to be significantly higher in IgAN patients (15.4±0.3 mg/mL in IgAN vs. 14.5±0.6 mg/mL in HC; P value<0.00001). Despite greater variability in the level of IgG in subjects with IgAN, there was no statistically significant difference in IgG levels (77.6±95.3 mg/ml in IgAN vs. 28.7±18.7 mg/ml in HC) by ELISA (p=0.1). There was also no significant difference between the IgG levels of progressors and non-progressors (p=0.17).

Immune Response Repertoire in IgAN

Figure 2:
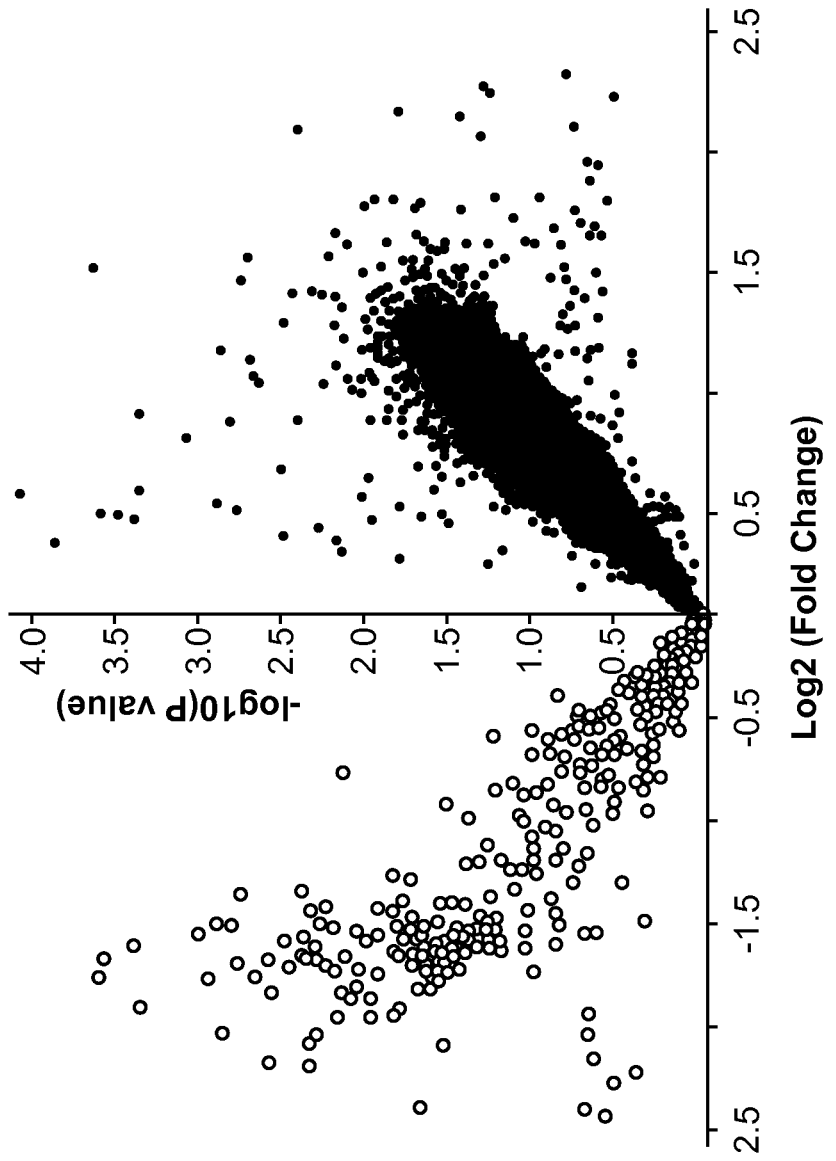
FIG. 2 shows a volcano plot that demonstrates immune response in terms of auto-antibodies in IgAN when compared to normal controls with 117 autoAbs were increased in IgAN with P value≤0.05. Each spot represents an autoantibody for a specific protein target.
Figure 3:
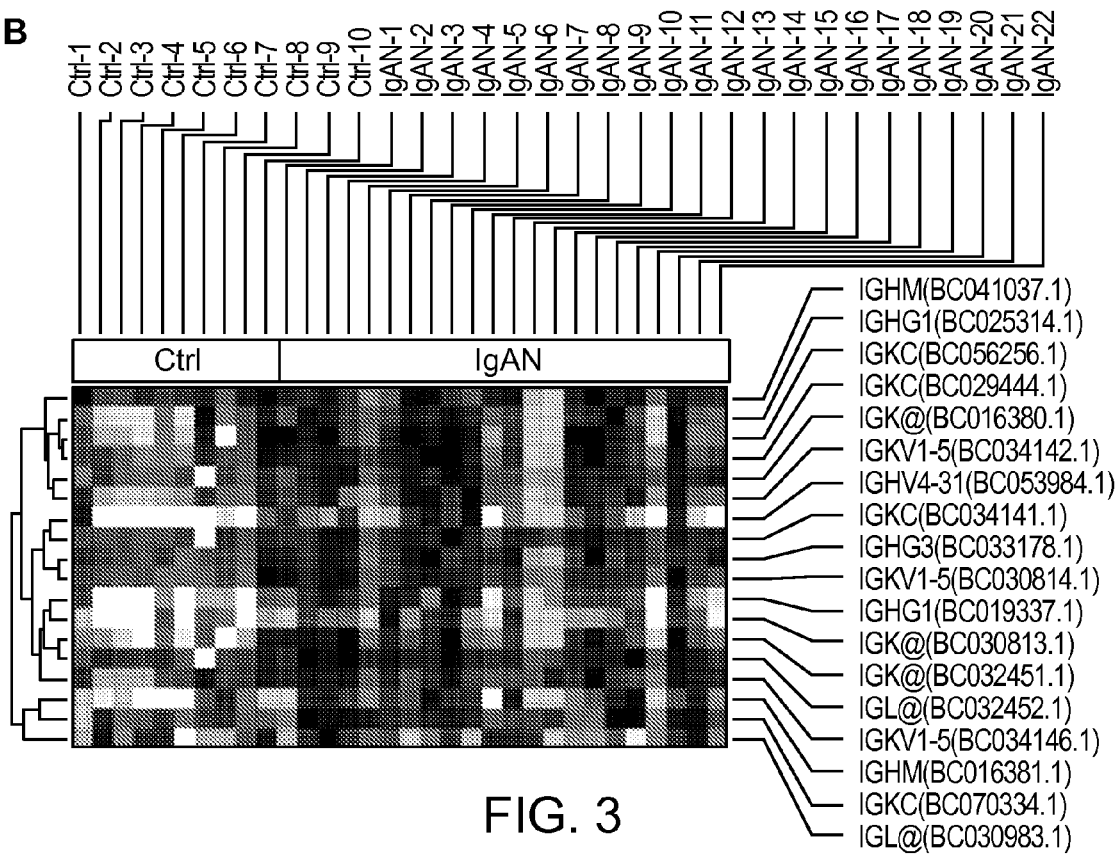
FIGS. 3A-B illustrate the increased reactivity against a number of immunoglobulins observed among IgAN patients. (A) The list of immunoglobulins significantly increased in sera of IgAN patients. (B) A heatmap that demonstrates separation of HC from IgAN patients based purely on the intensity of the different immunoglobulin responses in IgAN.

Based on the fluorescent intensity measured for the bound secondary Ab for each AutoAb, a set of 117 autoAbs were increased in IgAN sera (p≤0.05) and 28 were highly significant (p<0.01) (FIG. 2). Eighteen of these (15.4%) were related to different immunoglobulin classes (FIG. 3), such as immunoglobulin heavy constant gamma 1 (IGHG1), immunoglobulin heavy constant gamma 3 (IGHG3), immunoglobulin heavy constant mu (IGHM), immunoglobulin heavy variable 4-31 (IGHV4-31), immunoglobulin kappa constant (IGKC), immunoglobulin kappa variable 1-5 (IGKV1-5), and immunoglobulin lambda locus. Cluster analysis of the samples shows clear separation of IgAN and HC based on the detection of these different immunoglobulin reactivities in IgAN patients. Of the 117 autoAb in IgAN, 99 were mounted against non-immunoglobulin protein targets (Table 4).

Figure 4:
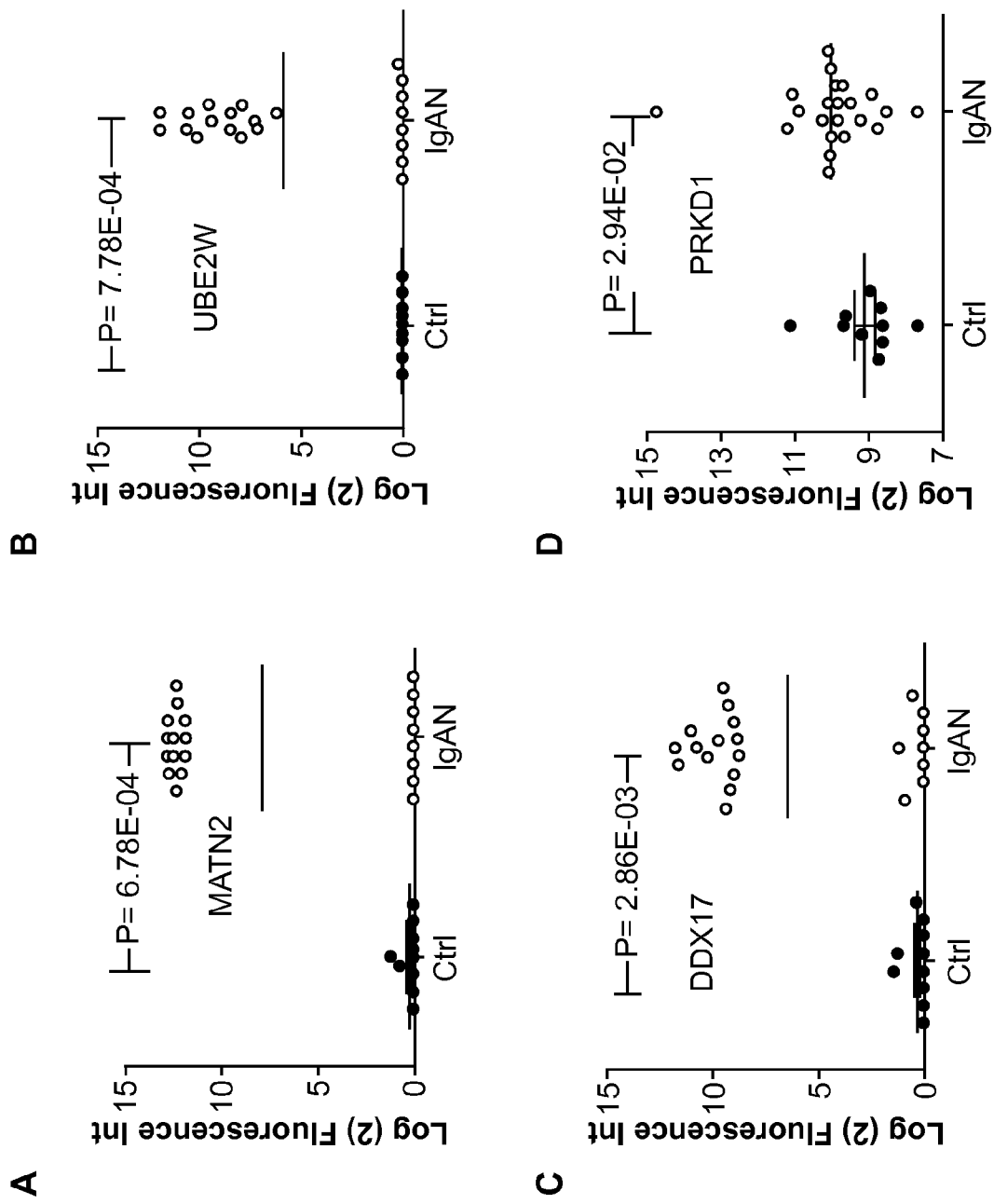
FIGS. 4A-D show scatter-plots for the MATN2, UBE2W, DDX17, and PRKD1 Abs that are increased in IgAN. A number of autoAbs were identified with a significant increase in reactivities against their targets (Table 4). Scatter-plots for antibodies of Matriline2 (MATN2) (A), Ubiquitin-conjugating enzyme E2W (UBE2W) (B), DEAD box protein (DDX17) (C), and Protein kinase D1 (PRKD1) (D) are shown in terms of their relative fluorescence intensities in HC and IgAN.

For a functional analysis of the non-immunoglobulin protein targets in IgAN, Pathway analysis (Ingenuity® Systems, Redwood City, Calif.) was used. This approach revealed that increased autoAb responses against CDKN1B and SOD2 proteins could alter their functions, known to be involved in mesangial cell apoptosis (Hiromura et al. "Modulation of apoptosis by the cyclin-dependent kinase inhibitor p27(Kip1)." J. Clin. Invest. 1999; 103: 597-604; Moreno-Manzano et al. "Selective involvement of superoxide anion, but not downstream compounds hydrogen peroxide and peroxynitrite, in tumor necrosis factor-alpha-induced apoptosis of rat mesangial cells." J. Biol. Chem. 2000; 275: 12684-12691). Furthermore, an analysis of the main functional classes by pathway analysis revealed that the most significant autoAbs were reactive against proteins involved in apoptosis (p≤0.05; 21 proteins), cellular assembly and organization (p<0.04; 20 proteins), and cellular development (p≤0.05; 19 proteins). These autoAb targets are also associated with dysregulation of proteins in immunologic disease (p≤0.045), connective tissue disorders (p≤0.045), and dermatological conditions (p≤0.045), reflecting some of the systems affected in IgA disease (Table 5). Other Ab targets were noted to include the cAMP responsive element modulator 1 (CREM), Fc fragment of IgG, low affinity IIIa receptor for (CD16) (FCGR3A), and CD79a molecule, immunoglobulin-associated alpha (CD79A), which have also been reported to be dysregulated in systemic lupus erythematosus (Juang et al. "Systemic lupus erythematosus serum IgG increases CREM binding to the IL-2 promoter and suppresses IL-2 production through CaMKIV." J. Clin. Invest. 2005; 115: 996-1005; Brambila-Tapia et al. "FCGR3A V(176) polymorphism for systemic lupus erythematosus susceptibility in Mexican population." Rheumatol. Int. 2010; Li et al. "B cell depletion with anti-CD79 mAbs ameliorates autoimmune disease in MRL/lpr mice." J. Immunol. 2008; 181: 2961-2972). Four of the most significantly elevated antibodies were against proteins found in or highly specific to the kidney. These were Matriline2 (MATN2) Ubiquitin-conjugating enzyme E2W (UBE2W), DEAD box protein (DDX17) and Protein kinase D1 (PRKD1). Signal differences for these four autoAb are shown for each individual patient and HC in FIG. 4.

TABLE 4

List of biologically relevant proteins with increased IgG antibodies in IgAN

| S. No. | Gene Symbol | Gene Name | Present in glom. (yes = X, data not available = na)* | Present in tubules. (yes = X, data not available = na)* | Highly kidney specific from gene expression data** | P-Value |
|---|---|---|---|---|---|---|
| 1 | PRKD1 | Serine/threonine-protein kinase D1 | X | X | X | 0.03 |
| 2 | MATN | Matrilin-2 | X | X | | <0.0 |
| 3 | DDX17 | DEAD(Asp-Glu-Ala-Asp) box polypeptide 17 2 | X | X | | <0.0 |
| 4 | UBE2 | ubiquitin-conjugating enzyme E2W | na | Na | X | 0.05 |
| 5 | CDKN1 | cyclin-dependent kinase inhibitor 1B | X | X | | 0.02 |
| 6 | SOD2 | superoxide dismutase 2, mitochondrial | X | X | | 0.05 |
| 7 | IQCK | IQ motif containing K | X | X | X | 0.05 |
| 8 | BLZF1 | basic leucine zipper nuclear factor 1 | X | X | | 0.02 |
| 9 | EFNA3 | ephrin-A3 | X | X | | 0.01 |
| 10 | EIF4A2 | eukaryotic translation initiation factor 4A | X | X | | 0.05 |
| 11 | FLII | flightless I homolog | X | X | | 0.05 |
| 12 | LIMCH | LIM and calponin homology domains 1 | X | X | | 0.05 |
| 13 | MAGE | melanoma antigen family A, 4 | X | X | | 0.05 |
| 14 | MEF2 | myocyte enhancer factor 2D | X | X | | 0.03 |

TABLE 4-continued

List of biologically relevant proteins with increased IgG antibodies in IgAN

| S. No. | Gene Symbol | Gene Name | Present in glom. (yes = X, data not available = na)* | Present in tubules. (yes = X, data not available = na)* | Highly kidney specific from gene expression data** | P-Value |
|---|---|---|---|---|---|---|
| 15 | MLLT6 | myeloid/lymphoid or mixed-lineage leukemia (trithorax homolog, *Drosophila*); translocated | X | X | | 0.02 |
| 16 | CIAPIN | cytokine induced apoptosis inhibitor 1 | na | Na | X | 0.05 |
| 17 | GDI2 | GDP dissociation inhibitor 2 | na | Na | X | 0.02 |
| 18 | HSPA8 | heat shock 70 kDa protein 8, transcript variant | | X | X | 0.05 |
| 19 | SERPI | serpin peptidase inhibitor, clade A (alpha-1 | na | Na | X | 0.05 |
| 20 | TGM1 | transglutaminase 1 (K polypeptide epidermal type I, protein-glutamine-gamma- | | X | X | 0.05 |

All the Auto-Abs for corresponding proteins were significantly increased in IgAN compared to HC (P ≤ 0.05)
*No IHC data available,
**with FDR <5%,
***

TABLE 5

Associated pathways and molecular functions for increased autoantibodies specific to IgA nephropathy

| Molecular Pathway/Function | Associated Antigens |
|---|---|
| Apoptosis | IGHG1, IGHG3, NEK2, TNS1, EDIL3, CDKN1B, ABCD1, KIFC3, HSPA8, RAB38, SOD2, TOM1, RASA1, AGAP1, CD7, IGHM, CKM, JAK3, SEPT5, BLZF1, and CDKN1B |
| Cellular assembly and organization | ABCD1, AGAP1, BLZF1, CD7, CDKN1B, CKM, EDIL3, HSPA8, IGHG1, IGHM, JAK3, KIFC3, NEK2, SEPT5, SOD2, TNS1, RASA1, IGHG3, TOM1, and RAB38 |
| Cellular development | CD79A, IGHG1, SART1, RASA1, EFNA3, GNAT2, MED6, CDKN1B, MEF2D, SOX5, CIAPIN1, IGHM, JAK3, NIF3L1, PRKD1, RBPJ, SOD2, TRPV4, and TGM1 |
| Immunologic disease | IGHM, IGKC, JAK3, CDKN1B, ALCAM, FCGR3A, and IGHG1 |
| Connective tissue disorders | TPRA1 |
| Dermatologic conditions | CD79A, IGHG3, IGHM, IGK@, IGL@, PLXNA1, HN1, IGHG1, IGKC, POLH, and TGM1 |

Immune Response Profiling of IgANp and IgANnp

When the increased autoAbs in IgAN were compared, autoAbs against 5 targets, primarily protein kinases, were significantly increased in the IgAN progressor group (IgANp) compared with the IgAN non-progressor group (IgANnp) (p value<0.05). The list includes (1) MAPK-interacting and spindle-stabilizing protein, SMITH (Sm) Antigen, (2) RIO kinase 3 (RIOK3), (3) protein tyrosine phosphatase type IVA, member 1, (PTP4A1), (4) leucine rich repeat containing 8 family, member D (LRRC8D), (5) and the death-associated protein kinase 3 (DAPK3). LRRC8D is present in glomeruli and renal tubules and is reported to be involved in cell cycle exit in T lymphoblasts by IL-2 withdrawal (Chechlinska et al. "Molecular signature of cell cycle exit induced in human T lymphoblasts by IL-2 withdrawal." BMC Genomics 2009; 10: 261; Berglund et al. "A genecentric Human Protein Atlas for expression profiles based on antibodies." Mol. Cell Proteomics 2008; 7: 2019-2027). RIOK3, reported to interact with caspase-10 and inhibit the NF-kappaB signaling pathway, is expressed in renal tubules (Shan et al. "RIOK3 interacts with caspase-10 and negatively regulates the NF-kappaB signaling pathway." Mol. Cell Biochem 2009; 332: 113-120).

Integrative Bioinformatics and Immunohistochemistry (IHC)

Publically available tissue specific gene expression data (Higgins et al. "Gene expression in the normal adult human kidney assessed by complementary DNA microarray." Mol. Biol. Cell 2004; 15: 649-656) was utilized to perform an integrative genomic and antibiomic analysis to predict which, if any, corresponding proteins to the 99 autoAb were highly expressed in the kidney, as these would be the most functionally relevant for the pathogenesis of IgAN (Li et al., ibid). 9 corresponding proteins were identified as highly expressed in kidney with FDR<5% (p=1.13E-5). The descriptions of these proteins are shown in Table 4. The kidney specific expression of all 99 proteins was examined using the publicly available immunohistochemistry data from Human Protein Atlas (www[dot]proteinatlas[dot]org) (Berglund et al. "A genecentric Human Protein Atlas for expression profiles based on antibodies." Mol. Cell Proteomics 2008; 7: 2019-2027). There was significant enrichment for antigens expressed in the glomeruli and tubules of the kidney (n=32; p<1 E-6) 18 and 15 additional proteins were only expressed in the renal tubules (p<1 E-6). A list of 20 biologically relevant antigenic targets and the information regarding their presence and location in the kidney b IHC is also provided in Table 4.

PRKD1 was chosen for IHC as it showed significant correlation with clinical variables. In addition, IGKC and UBE2W were chosen for IHC because previously published integrative genomics study showed high expression of these proteins in the kidney (Li et al., ibid). The IHC of PRKD1 showed weak patchy cytoplasmic staining within podocytes in a few biopsies of IgAN tissue. In addition, mildly increased immunostaining was observed within proximal and distal tubules, especially along the apical aspects (FIG. 5(i)b), however there was no significant staining in normal kidney tissue (FIG. 5(i)a).

Figure 5:
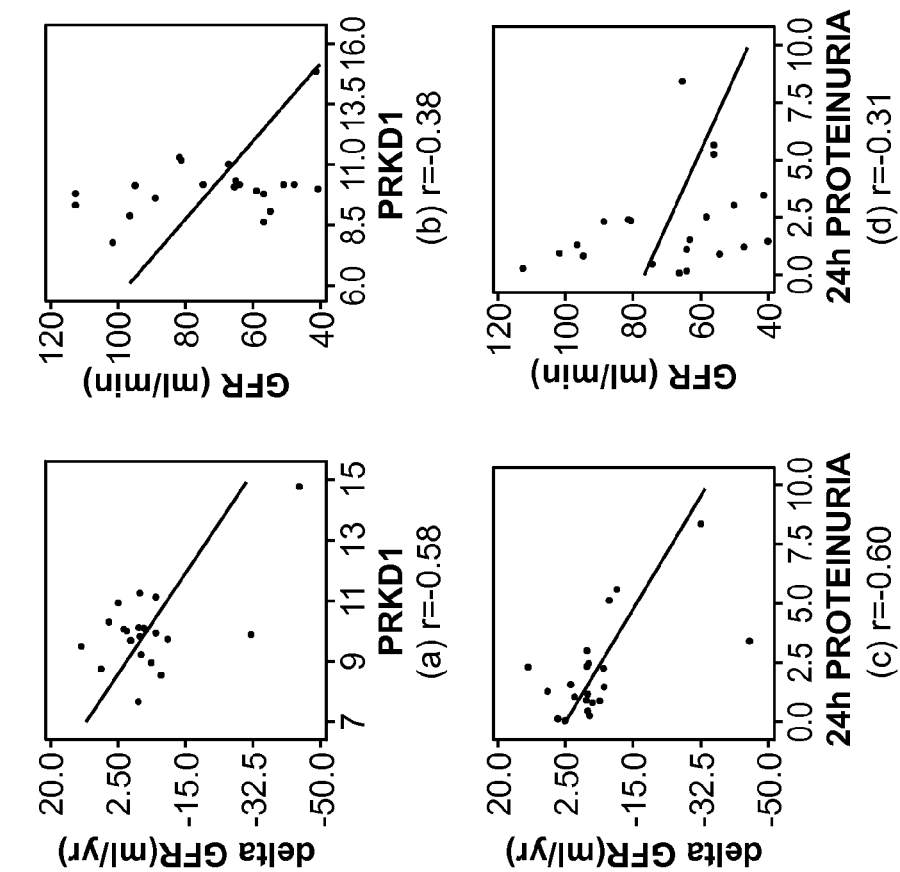
FIGS. 5A-F show immunohistochemical staining for PRKD1, IGKC, and UBE2W in normal kidney tissue and kidney tissue with IgA nephropathy. No significant staining for PRKD1, IGKC, and UBE2W was observed in glomeruli and tubules in normal kidney (a, c, e). However, there was a patchy staining within podocytes and increased staining within tubular cells for PRKD1 (b), Increased staining for IGKC in the glomerular endothelium and proximal tubules (d), and increased staining of proximal tubular region for UBE2W in kidney tissue with IgA nephropathy (f). Also shown are graphs (FIG. 5 right) that illustrate the level of PRKD1 antibody correlates with progression of IgAN.
Figure 5:
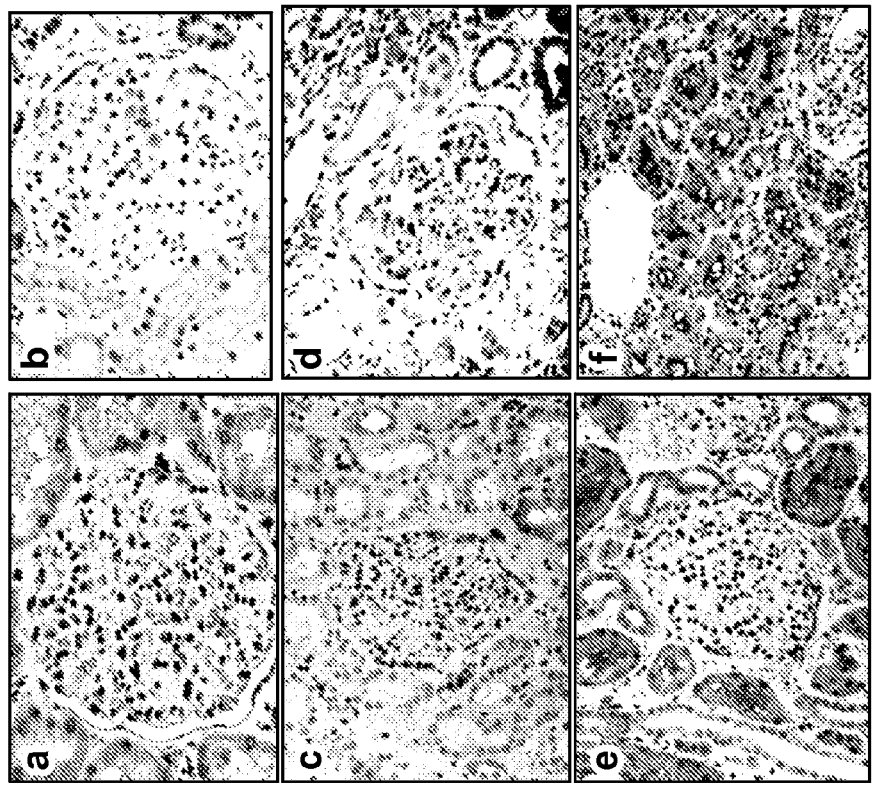

No significant staining for IGKC was observed in glomeruli and tubules in normal kidney and UBE2W staining revealed moderate granular cytoplasmic pattern in proximal tubules, but no staining in glomeruli (FIG. 5(i)c and FIG. 5(i)e). However, there was increased staining for IGKC in the glomerular endothelium and proximal tubules (FIG. 5(i)d) and increased staining for UBE2W in the proximal tubular cells with accentuation of the brush border in kidney tissue from patients with IgAN (FIG. 5(i)f).

Prediction of Renal Function Decline Using PRKD1 Ab and 24 Hr Proteinuria

The positive predictive value (PPV) and negative predictive value (NPV) of 24 hr proteinuria for the risk of ending up in the progressor group was 42.86% and 85.71%, respectively (a cut-off of positive 24 hr proteinuria being greater than 1 g per day). IgG autoAbs were investigated to see if they could predict the progression of IgA nephropathy or could be used in combination with 24 hr proteinuria, given the low PPV of 24 hr proteinuria.

Figure 6:
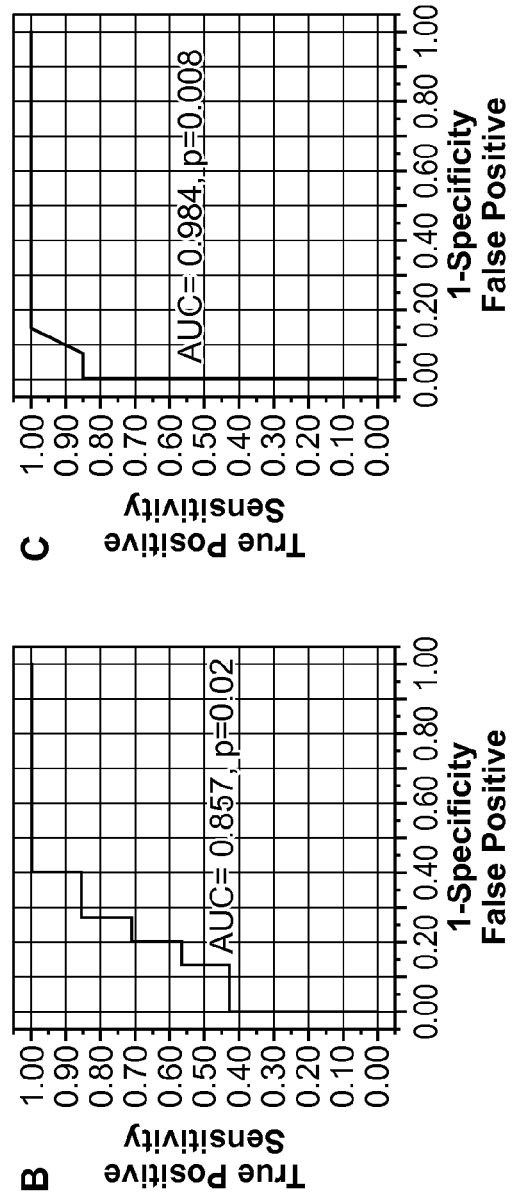
FIGS. 6A-C shows the results of linear regression analysis (A) and ROC analysis of 4 combined Abs (MATN2, UBE2W, DDX17, PRKD1) (B) and ROC analysis of 4 Abs and 24 hr proteinuria (C).

The signal intensity of IgG antibody against PRKD1 in IgAN significantly correlated with the observed decline of kidney function during the study (delta inulin GFR; R=−0.58; P. 0.004). The results of linear regression analyses between a decline of kidney function and clinical variables are shown in FIG. 6. By univariate analysis, there was no significant correlation of age at presentation, initial systolic blood pressure (SBP), diastolic blood pressure (DBP) or initial GFR with the subsequent decline in kidney function. The amount of 24 hour proteinuria at the study start correlated, as expected, with a decline in insulin GFR (R=−0.60; p=0.0038). In multivariate analysis, after adjusting for other clinical variables including age, SBP, DBP, hematocrit, and initial GFR, the intensity of the autoAb signal against PRKD1 correlated with a decline in kidney function even more significantly than the extent of proteinuria over 24 hours (Regression coefficient: −4.73 versus −2.72).

FIG. 6 (B) shows Receiver Operating Characteristic (ROC) curve analysis when the previously mentioned IgG antibodies (MATN2, UBE2W, DDX17, PRKD1) were used in combination. AUC was 0.857 (p=0.02) based on logistic regression model by combining the 4 antibodies' signal intensity if the arbitrary cutoff of −5 ml/yr renal function decline was used to diagnose the progressor and non-progessor. FIG. 6 (C) shows ROC curve analysis when the 4 Abs (MATN2, UBE2W, DDX17, PRKD1 specific) and 24 hr proteinuria were used in combination. AUC was 0.984 (p=0.0008) by performing logistic regression. AUC of 24 hr proteinuria alone was 0.816 (p=0.02). This finding suggests that using IgG autoAbs in addition to 24 hr proteinuria could improve the ability to predict the progression of disease.

Specificity of AutoAbs to IgAN

Protoarray analysis was done in a cohort of 15 patients with other glomerular diseases (membranous and FSGS) with a similar range of GFR and urine protein as our IgAN subjects. Their autoAB profile (data not shown) was distinct with only 6 of the autoAb overlapping the IgAN group as significantly increased, none of which included the autoABs of greatest significance. This suggests that the autoAb pattern is relatively specific to IgAN, at least as compared to other proteinuric glomerular diseases.

Conclusion

IgAN is associated with elevated IgG autoAbs to multiple proteins in the kidney. Anti PRKD1 was strongly correlated with the progression of kidney disease in IgAN. This analysis of the repertoire of autoAb in IgAN identifies, immunogenic protein targets, highly expressed in the kidney glomerulus and tubules that are of interest in the pathogenesis and progression of IgAN.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method for predicting the presence or absence of or progression of Immunoglobulin A nephropathy (IgAN) in a subject, the method comprising:
    measuring the level of one or more autoantibodies in a sample from the subject wherein the one or more autoantibodies is selected from autoantibodies specific for one or more of matrilin 2 (MATN2), ubiquitin-conjugating enzyme E2W (UBE2W), DEAD box protein 17 (DDX17) and protein kinase D1 (PRKD1);
    determining whether the subject has a IgAN phenotype based on the antibody signature, wherein the determining step is further based on the results of glomerular filtration rate testing or proteinuria testing; and
    providing the result of the determination in a user-readable format.

2. The method of claim 1, wherein the level of at least 5 autoantibodies specific for proteins from Table 1 is evaluated.

3. The method of claim 2, wherein the level of at least 10 autoantibodies specific for proteins from Table 1 is evaluated.

4. The method of claim 3, wherein the level of at least 15 autoantibodies specific for proteins from Table 1 is evaluated.

5. The method of claim 4, wherein autoantibodies specific for all of the proteins listed in Table 1 are evaluated.

6. The method of claim 1, wherein the sample is a serum.

7. The method of claim 1, wherein said determining step comprises comparing said antibody signature to a reference.

8. The method of claim 1, wherein the subject is determined to have IgAN when the level of the at least one autoantibody in the sample is increased as compared to a reference antibody signature.

9. The method of claim 1, wherein the evaluating step comprises a protein microarray assay.

10. The method of claim 1, wherein the autoantibodies are specific for proteins in one or more of the following categories: kidney proteins, glomerular proteins, tubular proteins, proteins involved in apoptosis, proteins involved in cell cycle regulation, and proteins involved in cellular assembly, or organization and/or cellular development.

11. The method according to claim 1, wherein the measuring is performed using a protein quantification protocol selected from the group consisting of an immunoassay, HPLC, mass spectrometry, LC-MS based peptide profiling, Multiple Reaction Monitoring, and a multiplex protein assay.

12. The method of claim 1, wherein the method comprises measuring the level of two or more autoantibodies.

* * * * *